United States Patent [19]

Mouwen

[11] 4,235,233

[45] Nov. 25, 1980

[54] BAG FOR COLLECTING, STORING AND ADMINISTERING INCLUDING FILTERING BLOOD, BLOOD COMPONENTS, INTRAVENOUS FLUIDS AND SIMILAR FLUIDS

[75] Inventor: Herman C. Mouwen, Ventura, Calif.

[73] Assignees: Johnson & Johnson, New Brunswick, N.J.; Purolator, Inc., Newbury Park, Calif.

[21] Appl. No.: 20,158

[22] Filed: Mar. 14, 1979

Related U.S. Application Data

[63] Continuation-in-part of Ser. No. 793,654, May 4, 1977, abandoned.

[51] Int. Cl.³ .............................................. A61M 5/00
[52] U.S. Cl. ................................ 128/214 D; 128/272; 210/DIG. 23; 150/2.5
[58] Field of Search ................... 128/272, 214 D, 760, 128/767, 768, DIG. 24; 210/DIG. 23, 446, 447; 206/219; 150/2.5

[56] References Cited

U.S. PATENT DOCUMENTS

| | | | |
|---|---|---|---|
| 1,308,427 | 7/1919 | Laburde | 150/2.5 |
| 2,842,122 | 7/1958 | Butler | 128/214 D |
| 2,848,995 | 8/1958 | Ryan | 128/214 D |
| 3,006,341 | 10/1961 | Poitras | 128/214 D |
| 3,175,558 | 3/1965 | Caillouette et al. | 206/219 |
| 3,257,072 | 6/1966 | Reynolds | 128/272 |
| 3,506,130 | 4/1970 | Shaye | 210/DIG. 23 |
| 3,744,625 | 7/1973 | Chin | 206/219 |
| 3,815,754 | 6/1974 | Rosenberg | 210/DIG. 23 |
| 4,035,304 | 7/1977 | Watanabe | 210/DIG. 23 |
| 4,066,556 | 1/1978 | Vaillancourt | 210/DIG. 23 |

FOREIGN PATENT DOCUMENTS 2276836 1/1976 France .................................. 128/214 D Primary Examiner—Robert W. Michell
Assistant Examiner—Arthur S. Rose
Attorney, Agent, or Firm—Robert L. Minier

[57] ABSTRACT

A bag for collecting, storing and administering medical fluids and having an integral filter for such fluids disposed at the bottom section of the bag in substantially a vertical plane to the flow of the fluid.

The present invention is directed to an improved medical fluid bag which incorporates an integral filter with said bag.

8 Claims, 8 Drawing Figures

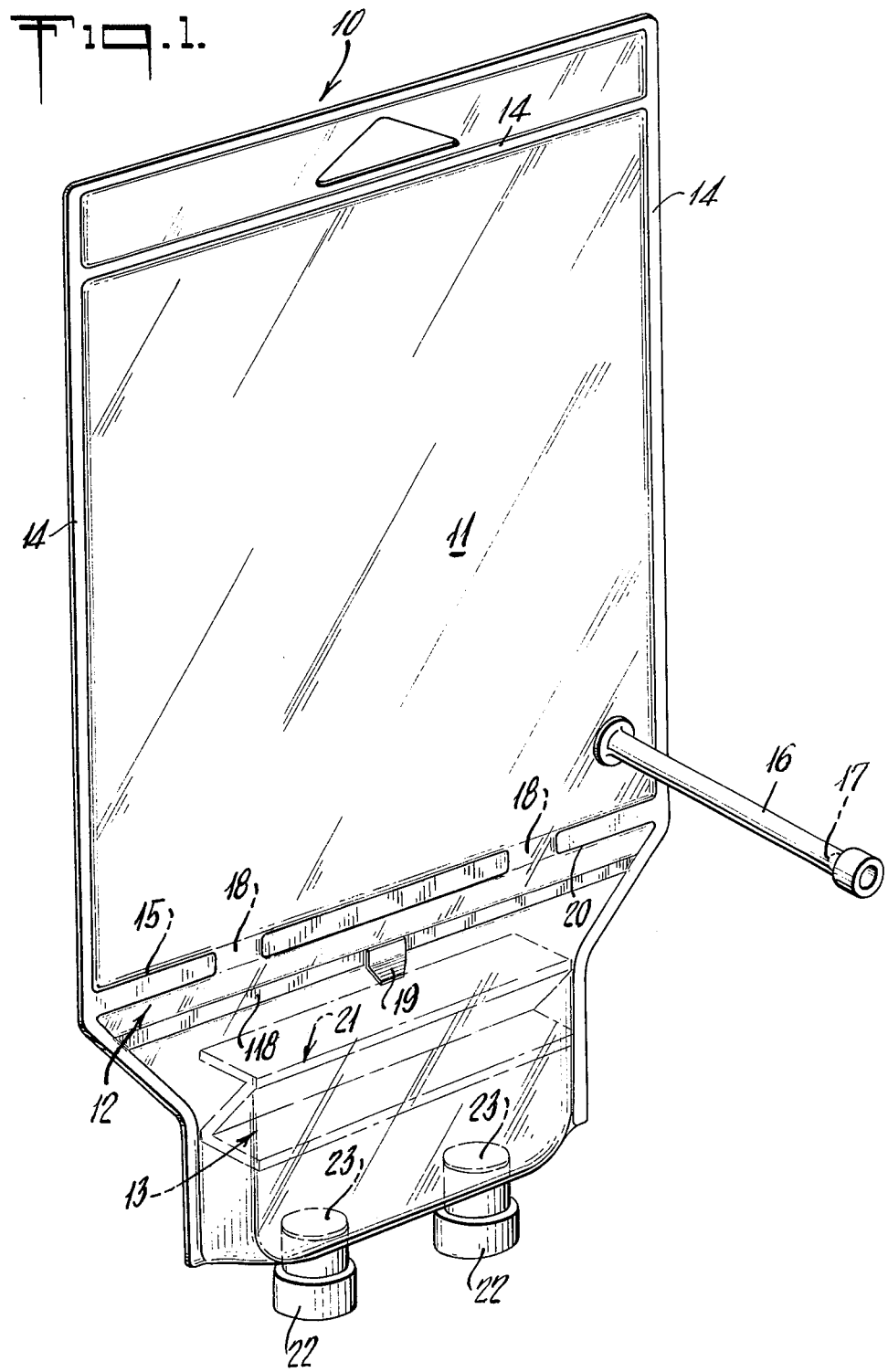

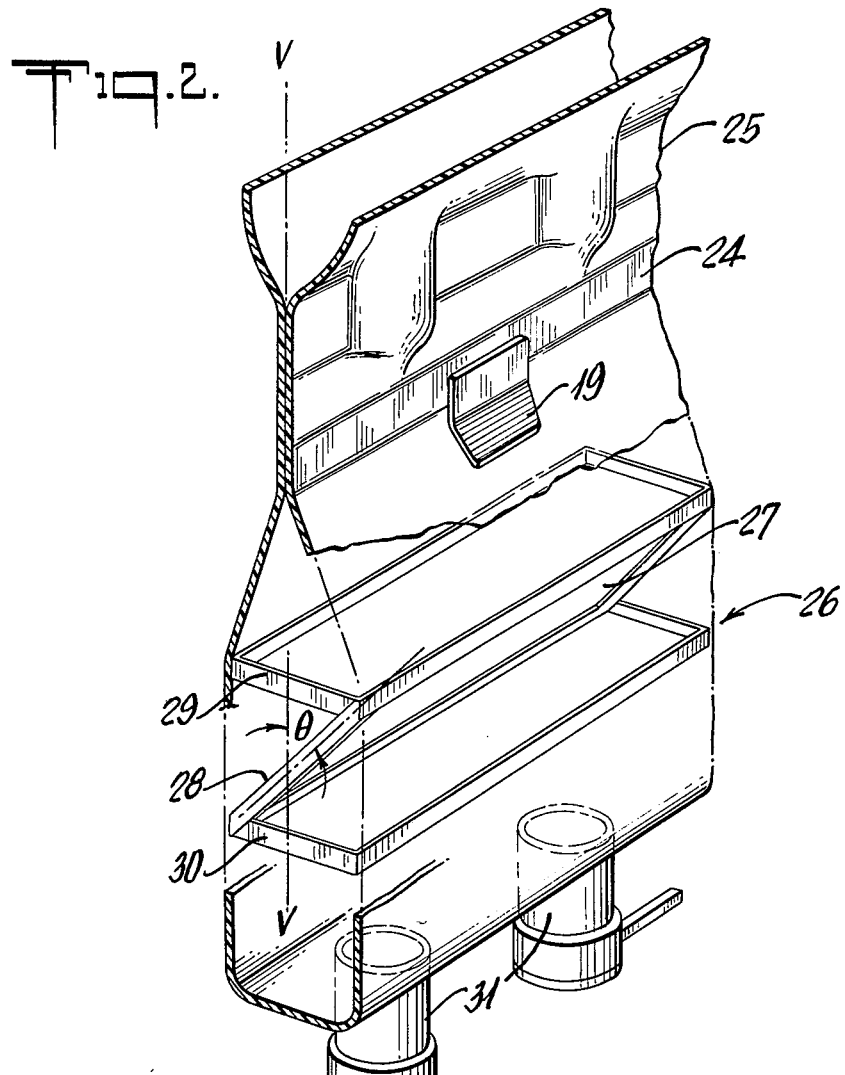
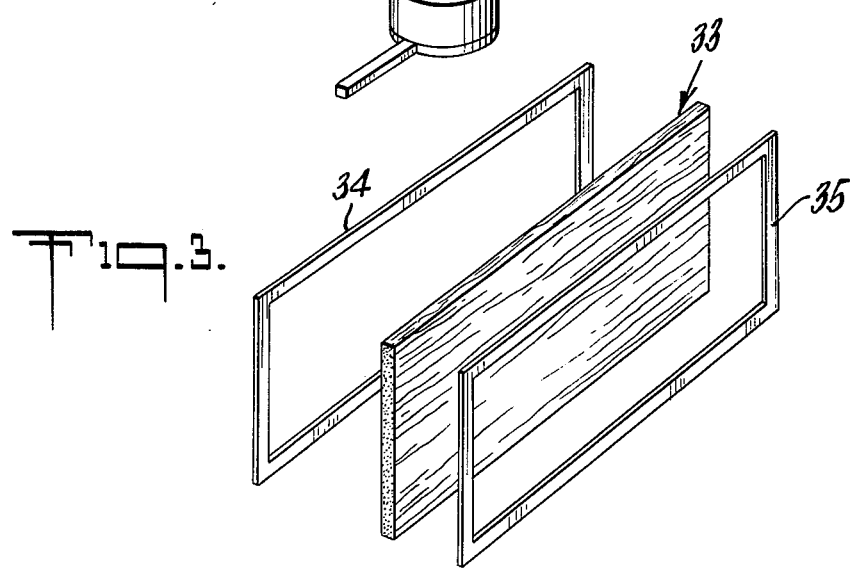

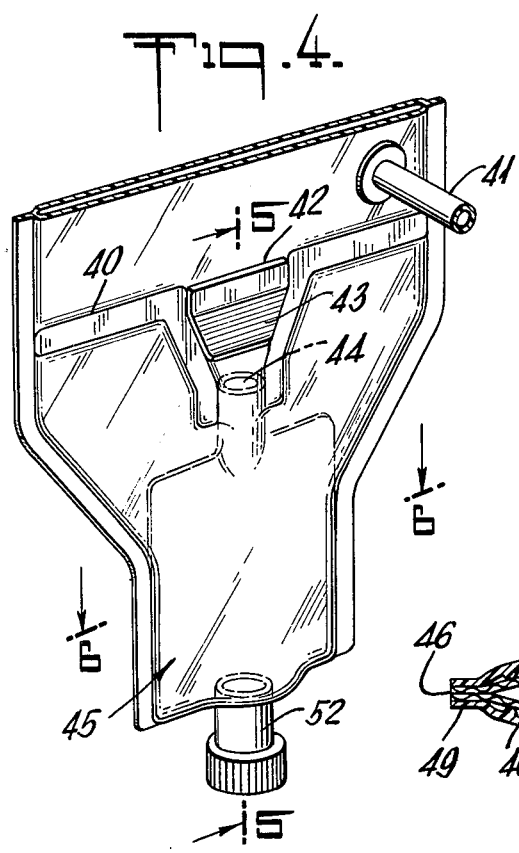
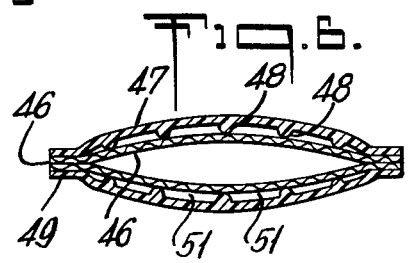
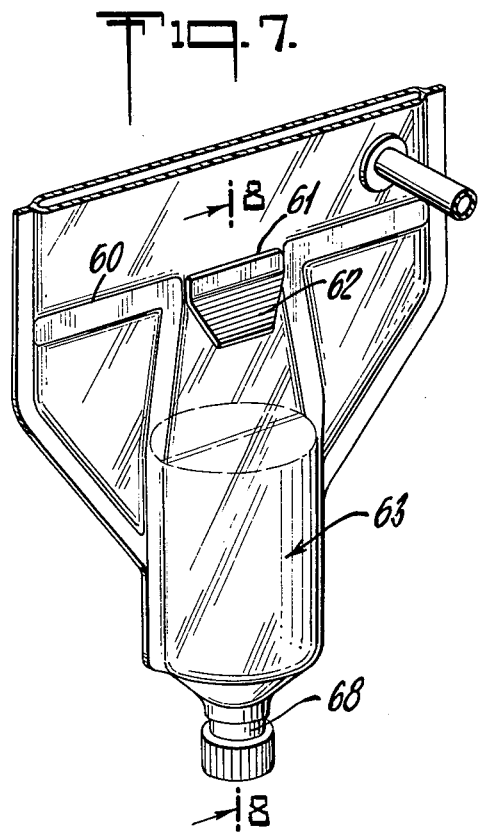
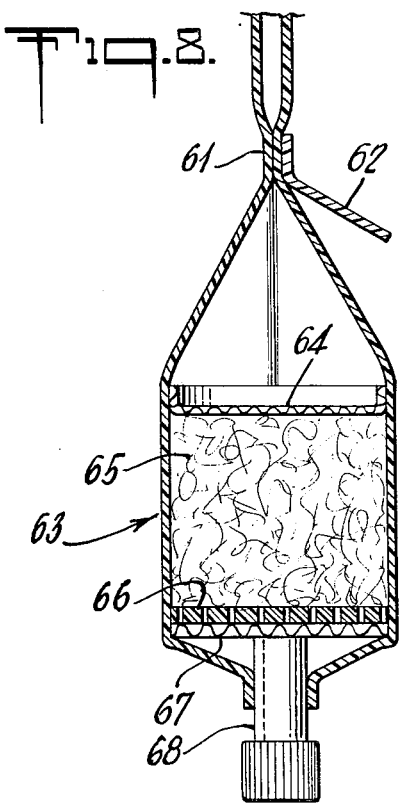

BAG FOR COLLECTING, STORING AND ADMINISTERING INCLUDING FILTERING BLOOD, BLOOD COMPONENTS, INTRAVENOUS FLUIDS AND SIMILAR FLUIDS

BACKGROUND OF THE INVENTION

This application is a continuation-in-part application of my co-pending application Ser. No. 793,654 filed May 4, 1977, now abandoned.

Though the present invention may be utilized with various types of medical fluids such as intravenous fluids of all types, blood and blood components, it will primarily be described in conjunction with its use with human blood in order to simplify the description.

In the storage and transfusion of human blood, the blood is usually taken from the donor and placed in a sterile plastic bag. The bag containing the blood may then be stored for a short period of time up to approximately twenty-one days under refrigeration. When the blood is to be administered to a patient in the form of a blood transfusion, an administration set is placed on the bag usually along with some type of filter. The blood is allowed to flow through the filter by gravity and slowly administered to the patient. Generally the filters used in such blood transfusions are designed to filter up to five units or five pints of blood. This is done because very often one patient may require more than one unit of blood at any given time. However, in many instances patients may require only one or two units of blood and, hence, the use of such an overdesigned filter may be inefficient and uneconomical. Furthermore, in the prior art, use of separate blood bags and separate filters it is required that the filter be sterilized separately and, of course, with the necessity for handling the filter and inserting it into the blood bag, etc., the possibility of contamination, the loss of sterility, and an additional leak path is always present.

Though intravenous fluid filters have been designed for smaller dosage units and, hence, do not suffer from the problem of inefficient use nearly as much as blood filters, they still require the extra handling and sterilization thereof and have the possible contamination problem.

SUMMARY OF THE INVENTION

What I have discovered is an improved medical fluid bag which incorporates, integral with the bag, a suitable filter for the fluid being held and stored by the bag. My improved filter is designed for the capacity of the fluid to be held by the bag and, hence, I make extremely efficient use of the filter media itself.

My improved bag and filter allows for relatively rapid filtration of fluids with a minimum of blockage of the filter media and also allows for the filtration to occur immediately prior to the fluid being administered to the patient.

The construction of my improved bag and filter and when used with blood keeps the traumatic effect caused by the handling of blood to a minimum and, hence, causes a minimum of hemolysis or other detrimental effects to the blood.

The bag and filter may be sterilized as one unit and, hence, the possibility of contamination during the handling and the use of my new bag and integral filter is greatly reduced and a potential leak path is eliminated. My improved bag and filter is used to accept, store, hold, filter and administer blood and other medical fluids.

In accordance with the present invention, my bag for collecting, storing and filtering blood, intravenous and similar fluids is a bag which is sealed about its periphery. The bag comprises an upper portion, a center portion and a lower portion.

The upper portion of the bag is an air-tight fluid storage section. The upper portion includes means for filling this portion with the desired medical fluid. When the bag is to be used for blood, the upper portion may include an integral blood donor tube. The tube is connected to the upper portion via an air-tight seal and may have connected at its other end a suitable sterile needle and enclosure. Such an integral donor tube allows the needle to be inserted in a patient and the upper portion of my new bag to be filled with donated blood and eliminate all handling during transfer of the blood.

A portion of the periphery of the upper portion is contiguous with the center portion of the bag. The center portion comprises at least one opening which communicates between the upper portion and the lower portion of the bag. If desired, there may be a plurality of openings in the central portion which communicate between the upper and lower portion of the bag. The openings in the center portion are temporarily sealed to prevent flow of fluid between the upper and lower portions. Disposed on the outside surface of the bag and communicating with the center portion are means for breaking the temporary seal at a desired time to allow for the flow of fluid through the openings into the lower portion.

The lower portion of the bag is contiguous with the center portion on the side opposite the upper portion. The lower portion includes suitable filter media for filtering medical fluid held in the upper portion.

The media is disposed at an angle of less than 45° to the primary plane of the bag and preferably at an angle of from 15° to 30° to said plane of the bag. The lower portion also includes a temporarily sealed outlet for allowing the insertion of an administration set to administer the filtered fluid to a patient. This outlet is disposed on the side of the filter media opposite the opening in the center portion. The media is sealed about its edges so that all fluid flowing from the upper portion through the center portion to the administering outlet is filtered by the media.

DESCRIPTION OF THE DRAWINGS

The invention will be more fully described in conjunction with the accompanying drawings wherein:

FIG. 1 is a view in perspective of the new blood bag and integral filter of the present invention;

FIG. 2 is an expanded blown-up view of the openings in the center portion, fully opened along with the filter in the lower portion of the blood bag of the present invention;

FIG. 3 is an expanded view of the filter and the means for sealing the filter media used in the bag of the present invention;

FIG. 4 is a view in perspective of another embodiment of the blood bag and integral filter of the present invention with only the center and bottom portions being shown;

FIG. 5 is an enlarged cross-sectional view taken along line 5—5 of FIG. 4;

FIG. 6 is an enlarged cross-sectional view taken along line 6—6 of FIG. 4;

FIG. 7 is a view in perspective of another embodiment of the blood bag and integral filter of the present invention with the top or storage portion omitted;

FIG. 8 is an enlarged cross-sectional view taken along line 8—8 of FIG. 7.

DETAILED DESCRIPTION OF THE INVENTION

Referring to the drawings in FIG. 1 there is shown a new and improved bag 10 of the present invention. The bag comprises an upper portion 11, a center portion 12 and a lower portion 13. The upper portion of the bag is an air-tight fluid storage section. The upper portion is sealed 14 around three sides at the periphery of the bag. The fourth side 15 of the upper portion is contiguous with the center portion of the bag. Communicating with the upper portion is an outlet 16. This is a donor inlet and contains a temporary seal 17 which can be punctured by a suitable administration set or it may be directly connected to a donor set through a tube leading to a suitable needle in a standard type enclosure.

As previously mentioned, the fourth side 15 of the upper portion is contiguous with the center portion 12 of the bag. The center portion comprises a plurality of openings 18. Just below the openings is a temporary seal 118 and means 19 disposed on the outside surface of the bag for breaking the temporary seal.

Contiguous with the opposite side 20 of the center portion is the lower portion 13 of the blood bag. The lower portion of the bag comprises a filter 21 disposed in the line of flow of blood. On the opposite side of this media are suitable outlets 22 for connecting administration sets to the bag when the blood or similar fluid is to be administered to a patient. The openings contain temporary seals 23 which may be readily ruptured by the insertion of an administration set as is standard in the art.

The center and lower portions of the bag of the present invention are more clearly shown in FIG. 2. In FIG. 2 the temporary seal 24 in the center portion 25 may be broken so that the openings communicate directly with the lower portion 26. As may be seen in the Figure, the filter media 27 is in a "Z" type frame and is disposed along the diagonal 28 of the "Z". The upper leg 29 of the "Z" maintains the bag open to accept fluid through the openings from the center portion. The media itself is disposed on the diagonal of the "Z" and the bottom leg 30 of the "Z" also is used to maintain the bag open. The fluid flows through the openings to the filter media, is filtered thereby and then flows to the appropriate outlets 31 at the bottom of the bag. As may be seen, the media itself is disposed in substantially a vertical plane V—V or in the same major plane as the blood bag. The media is at an angle $\theta$ of less than 45°. By maintaining such an angle $\theta$ of less than 45°, rapid filtration is possible with a minimum of blockage of the media. Furthermore, by maintaining such an angle the traumatic effects or other harmful effects that are caused by the handling of blood are kept to a minimum.

In the preferred embodiments of the product of the present invention the filter media is disposed at an angle of from 15° to 30° to the major plane of the blood bag.

By positioning the filter media as shown and described, particles of blood, which may agglomerate are allowed to flow down to the bottom of the media and not block the media and prevent or reduce effective filtration area.

If the filter media is disposed at an angle greater than 45° to the primary plane of the bag, particles of blood may agglomerate on the filter surface and reduce filter efficiency. Also, angles of greater than 45° increase the width of the product and complicate the desired sterile packaging of the product. While angles of less than 15° simplify the packaging problems and help keep the filter surface free of agglomerates, such angles do not allow for the needed open volume on the upstream and downstream sides of the filter media, for satisfactory filter efficiencies, without some sort of support to keep the bag walls separated from the media.

As may be seen in FIG. 3, for ease of manufacture and assembly the media 33 itself may be disposed between two frame sections 34 and 35 and sealed to these frame sections about the periphery of the media to produce a tight, leak-proof seal.

The temporary seals in the center portion may be accomplished merely by lightly heat sealing plastic materials together. Tabs are disposed on either one or both outer surfaces of the bag. When these tabs are pulled away from each other, the temporary seal in the center portion is broken. This is only done when the bag is to be used for transfusing the medical fluid to the patient. The outside surface seal may also include a safety tab feature wherein it is strapped down so that one can be certain the seal has not been broken prior to administration of the fluid to the patient.

The openings in the lower portion of the bag may contain suitable administration sets or they may just contain rupturable diaphragms for insertion of the administration sets as is well known in the art.

Referring to FIG. 4 of the drawings there is shown another embodiment of the blood bag and integral filter of the present invention.

The blood bag is similar to that shown in FIG. 1 in that it has an air-tight fluid storage section. The upper portion is sealed around three sides of the periphery of the bag. The fourth side 40 is contiguous with the filter portion of the bag. A donor inlet 41 communicates with the upper portion of the bag for filling the bag with donated blood. The storage portion is separated from the filter portion by a temporarily sealed outlet 42. This seal may be broken by pulling the tab 43 apart to open the opening 44 into the filter unit 45. As is more clearly seen in FIGS. 5 and 6, the filter media 46 has an oval or circular cross-section and is held from the surface 47 of the bag by the spacers 48 as shown. As shown in FIG. 5, the media is folded or sealed at its lower end 53. The filter media 46 is also sealed along with the edges 49 of the bag as shown in FIG. 6. The flow of blood is through the opening into the center of the filter media out through the filter media in between the areas 51 between the media and the bag to the outlet 52 for administration to the patient.

The embodiment shown in FIGS. 7 and 8 is similar to that depicted in FIG. 4 with the exception that a different type of filter media is used. A depth type laminated media is used in the embodiment shown in FIGS. 7 and 8.

As may be seen in the drawings, the blood-holding portion is sealed from the filter portion along a line 60. There is a temporarily sealed opening 61 in the line. This seal may be broken by pulling the tab 62 which will present the blood to the filter section 63.

As mentioned above, instead of the substantially vertical filter media used in the previous embodiments, the embodiment depicted in FIGS. 7 and 8 uses a depth type filter media. The filter comprises a plurality of media stacked in a vertical configuration.

The uppermost or first media 64 is a clotting screen having a pore size opening of 170 micron to 200 micron. Beneath this media is a batt 65 of polyester fibers which has a pore size rating of about 16 to 50 microns. Below the batt is a polyester needle-punched disc 66 about ¼ inch thick and a 20 micron woven nylon mesh screen 67 to prevent any migration of the fibers to the blood outlet 68.

The materials used to manufacture the blood bags of the present invention may be any of the well known materials which are inert to blood and intravenous solutions as desired. Examples of suitable materials are the polyvinyl chlorides, polyethylene, polypropylene and the like.

The filter media used may vary depending on the solution to be filtered. For example, when human blood is to be filtered, it is found that medias having a 20 to 50 micron pore size rating have been found suitable; whereas, when filtering intravenous solutions much smaller pore sizes of down to 0.02 micron may be used. The media itself should be made of materials that are inert to blood or intravenous solutions such as the polyesters, nylons and the like.

As previously mentioned, it is important in the present invention when using a single filter media sheet, the media not be perpendicular to the flow of the blood but be at an angle and be as close to the vertical or the primary plane of the bag as reasonably possible. This is important to prevent blockage of the filter media during use. It is believed that by placing the media in this position, particles and globules being filtered will fall down to the edge of the filter and, hence, will not block off portions of the media.

Also as previously mentioned, once my bag and filter media is fully assembled, it may then be sterilized by any suitable sterilization techniques such as ethylene oxide, radiation, steam sterilization, etc. This may be accomplished in one operation and the unit fully sterilized prior to its use, that is, being filled with donated blood and being used to administer the medical fluid to the patient.

In manufacturing my new bag, the media is initially sealed about its periphery on both surfaces of the media in a frame. The media and frame is sealed along each long side to open rectangular frames which form the legs of the "Z" as shown in FIG. 2.

Suitable administration set openings and donor openings are also sub-assembled and these sub-assemblies are positioned appropriately on a polyvinyl chloride or similar sheet. The sheet is folded over on itself and ultrasonically sealed about its entire periphery and at appropriate points including the temporary seal of the center portion. This sealing may be accomplished by ultrasonic sealing using a rotary head. The appropriate administration set and donor set may then be attached to the bag.

Having thus described the invention, it should be readily apparent to one skilled in the art of the various modifications and alterations that may be made to the present invention. I desire to be limited only to the following claims.

I claim:

1. A bag for collecting, storing and filtering blood, intravenous and similar fluids, said bag being sealed about is periphery and comprising an upper, center and lower portions, said upper portion being an air-tight fluid storage section including means for filling said upper portion with the desired fluid, a portion of the periphery of said upper portion being contiguous with said center portion, said center portion comprising at least one opening extending between said upper portion and the lower portion of the bag, said opening being temporarily sealed to prevent the flow of fluid from the upper portion to the lower portion, means on the outside of the bag for breaking said temporary seal to allow flow of fluid to said opening and into the lower portion, said lower portion being contiguous to the center portion on the side opposite said upper portion, a substantially flat piece of filter media mounted in said lower portion, said filter media extending substantially the entire width of said lower portion and being disposed at an angle of less than 45 degrees to the primary plane of the bag, whereby fluids may be rapidly filtered with a minimum of blocking of the filter media, and said lower portion of said bag having an outlet for administering the fluid to a patient, said outlet being disposed on the side of the filter media opposite the opening in the center portion whereby the fluid administered from said bag may be filtered immediately prior to administration.

2. A bag according to claim 1 wherein the filter media is disposed at an angle of from 15 to 30 degrees to the primary plane of the bag.

3. A bag according to claim 2 wherein the upper portion includes an integral donor tube for filling said upper portion with donated blood.

4. A bag according to claim 2 wherein the center portion has a plurality of openings communicating between said upper portion and lower portion of the bag.

5. A bag according to claim 2 wherein the center portion has a plurality of openings communicating between said upper and lower portions and the filter media has a pore size rating of from 20 to 50 microns.

6. A bag according to claim 2 including an administration set attached to the lower portion of the bag.

7. The bag according to claim 1 wherein the media in the lower portion of the bag has a pore size rating of from 20 to 50 microns.

8. A bag according to claim 1 wherein the filter media in the lower portion of the bag has a pore size rating of from 0.2 to 0.5 microns.

* * * * *